United States Patent
Gotz et al.

(10) Patent No.: US 11,346,802 B2
(45) Date of Patent: May 31, 2022

(54) MEASURING ASSEMBLY FOR MEASURING LIQUIDS

(71) Applicant: Testo SE & Co. KGaA, Lenzkirch (DE)

(72) Inventors: Meinrad Gotz, Bonndorf (DE); Markus Munzer, Hufingen (DE); Siegfried Stallmann, Bonndorf (DE)

(73) Assignee: Testo SE & Co. KGaA, Lenzkirch (DE)

( * ) Notice: Subject to any disclaimer, the term of this patent is extended or adjusted under 35 U.S.C. 154(b) by 255 days.

(21) Appl. No.: 16/605,996

(22) PCT Filed: Apr. 26, 2018

(86) PCT No.: PCT/EP2018/060790
§ 371 (c)(1),
(2) Date: Oct. 17, 2019

(87) PCT Pub. No.: WO2018/197637
PCT Pub. Date: Nov. 1, 2018

(65) Prior Publication Data
US 2021/0140909 A1    May 13, 2021

(30) Foreign Application Priority Data
Apr. 28, 2017    (DE) .......................... 102017109225.0

(51) Int. Cl.
*G01N 27/22*    (2006.01)
*G01N 33/03*    (2006.01)

(52) U.S. Cl.
CPC ........... *G01N 27/228* (2013.01); *G01N 33/03* (2013.01)

(58) Field of Classification Search
CPC .................................................. G01N 27/228
(Continued)

(56) References Cited

U.S. PATENT DOCUMENTS

| 3,826,979 A | 7/1974 | Steinmann |
| 6,586,949 B1 | 7/2003 | Sargent et al. |
| (Continued) | | |

FOREIGN PATENT DOCUMENTS

| CN | 1179828 | 4/1998 |
| CN | 1846116 | 10/2006 |
| (Continued) | | |

OTHER PUBLICATIONS

Fiering, J.O. et al., "Manipulation of Microenvironment with a Built-in Electrochemical Actuator in Proximity of a Dissolved Oxygen Microsensor", Missouri University of Science and Technology—Scholars' Mine, IEEE Sensor Journal, IEEE Service Center, New York, NY, vol. 4, No. 5, Oct. 5, 2004, pp. 568-575.

*Primary Examiner* — Walter L Lindsay, Jr.
*Assistant Examiner* — Philipmarcus T Fadul
(74) *Attorney, Agent, or Firm* — Volpe Koenig

(57) ABSTRACT

To increase the measuring precision of an electric measuring assembly (1) for capacitively measuring a liquid, an inner electrode (2) and an outer electrode (3) arranged concentrically to the inner electrode is provided, in which a shielding electrode (5) is arranged between the outer electrode (3) and the inner electrode (2). The potential of the shielding electrode (5) can be actively adjusted to the potential of the inner electrode (2) by a corresponding electric connection such that electric fields which are caused by dielectric displacements in parasitic capacitances are effectively shielded from the inner electrode (2) and thus from the capacitance to be measured. For this purpose, a two-part design of the inner electrode (2) is provided with sections (6) and (7) which can be moved axially relative to each other.

22 Claims, 2 Drawing Sheets

(58) Field of Classification Search
USPC .......................................................... 73/53.01
See application file for complete search history.

(56) References Cited

U.S. PATENT DOCUMENTS

| | | |
|---|---|---|
| 2005/0173820 A1 | 8/2005 | Schneider et al. |
| 2009/0267619 A1 | 10/2009 | Slezak et al. |
| 2012/0092025 A1 | 4/2012 | Volker et al. |
| 2015/0285777 A1 | 10/2015 | Baumann et al. |
| 2015/0346136 A1 | 12/2015 | Kato |
| 2017/0292902 A1* | 10/2017 | Bardapurkar .......... G01N 13/00 |

FOREIGN PATENT DOCUMENTS

| | | | |
|---|---|---|---|
| CN | 106225876 | 12/2016 | |
| DE | 2239359 | 2/1974 | |
| DE | 3201799 | 8/1983 | |
| DE | 8707954 | 10/1988 | |
| DE | 102005043107 | 3/2007 | |
| DE | 19681725 | 4/2007 | |
| DE | 102010042637 | 4/2012 | |
| EP | 2937692 | 10/2015 | |
| WO | WO-0142774 A2 * | 6/2001 | ......... G01N 27/4473 |

\* cited by examiner

MEASURING ASSEMBLY FOR MEASURING LIQUIDS

BACKGROUND

The invention relates to an electrical measuring assembly for the capacitive measurement of a liquid, having an inner electrode which is arranged concentrically to a surrounding outer electrode, and having an insulating element which electrically insulates the inner electrode from the outer electrode.

Measuring assemblies of this type are known, and are employed, for example, in commercial kitchens, in order to determine the quality of frying oils and/or frying fats used in fryers. This is because as the service life of a frying oil or frying fat is prolonged, individual molecules of said oil or fat undergo breakdown. This depletion or ageing process is manifested by a change in the electrical properties of the oil or fat. Specifically, an increase in the electrical permittivity $\varepsilon$ of the oil or fat occurs, which is also described as dielectric conductivity.

Using a measuring assembly of the abovementioned type, such a variation in the permittivity $\varepsilon$ of the oil or fat can be determined as a characteristic variable for an alteration or ageing of said oil or fat: in measuring assemblies of this type, the capacitance to be measured is constituted between the centrally-arranged inner electrode and the surrounding outer electrode, wherein a geometrical center of the outer electrode typically coincides with that of the inner electrode. The oil or fat to be measured fills an interspace between the inner and outer electrodes, and thus functions as a dielectric for the capacitance to be measured.

This fundamental measuring method, and thus also the present invention, is applicable for the measurement of all such fluids which show a variable permittivity.

As a result of temperature variations, specifically during the heat-up of the oil or fat, mechanical stresses or strains can occur in the electrodes, which are typically constituted of a metal. This can result in a change in the effective clearance between the electrodes, which critically influences the capacitance to be measured. In the majority of applications, such a temperature-dependent variation in capacitance constitutes a disturbance variable, which must be eliminated by temperature compensation. By the application of temperature compensation, it is thus possible to determine the actual variable to be measured, namely, the variation in the permittivity of the liquid to be measured, even in the event of a changing liquid temperature, by reference to a (temperature-compensated) variation in the capacitance to be measured.

However, further disturbance variables occur, which can result in a defective measurement of the permittivity $\varepsilon$ of the oil or fat. For example, temperature variations in electrical insulation, specifically where the latter is constituted of plastic and the temperature of the liquid to measured achieves the glass transition temperature of said plastic, can result in abrupt changes in the permittivity of electrical insulation. A similar effect can occur in the event of the diffusion of water into the insulation, which can also occur in ceramic insulators and, for example, during the deep-frying of frozen food products. In known measuring assemblies from the prior art, these effects result in defective measurements, as stray capacitances occur between the inner electrode and the outer electrode, conveyed by the insulation, which vary in the event of changes in the permittivity of said insulation, and thus generate a measuring signal which is not dictated by a variation in the permittivity $\varepsilon$ of the fluid to be measured.

SUMMARY

The object of the invention is therefore the provision of a measuring device of the abovementioned type, with improved accuracy of measurement.

For the fulfillment of this object, in an electrical measuring assembly, one or more features according to the invention are provided. Thus, specifically, for the fulfillment of the object, in an electrical measuring assembly of the abovementioned type it is provided, according to the invention, that a shielding electrode is arranged between the inner electrode and the insulating element, which shields the inner electrode from the insulating element. This is advantageous, in that stray capacitances which, in the absence of the shielding electrode, and specifically conveyed by the insulating element, can be constituted between the inner electrode and the outer electrode, are suppressed.

The invention thus acknowledges that, for the achievement of a high accuracy of measurement, it is necessary for stray capacitances to be suppressed insofar as possible. Thus, the measuring assembly cannot initially distinguish a variation in a stray capacitance from a variation in the permittivity of the liquid to be measured, and thus a variation in the capacitance between the inner and outer electrodes. Varying stray capacitances generate measuring errors as a result.

In the absence of the employment of a shielding electrode, such a stray capacitance would exist, for example, between the inner electrode and the outer electrode, with the insulating element acting as an intermediary dielectric. Specifically in the event of the penetration of water into the insulating element, or in the event of temperature variations, the permittivity of the insulating element can change, inevitably resulting in a defective measuring signal. By the employment of the shielding electrode, this stray capacitance, although still present, exists between the shielding electrode and the outer electrode, whereas the inner electrode is isolated from the influence of the insulating element. Accordingly, variations in the permittivity of the insulating element can no longer impact upon the capacitance to be measured between the inner and outer electrodes.

In other words, by use of the invention, dielectric displacements in the insulation of the measuring assembly, specifically in the insulating element, will not result in a variation in the potential of the inner electrode and/or in a charge displacement on the inner electrode. This shielding of the inner electrode against interference effects in the insulation of the measuring assembly is achieved by the shielding electrode, which protects the inner electrode from electric fields which originate from the insulation.

By use of a measuring assembly according to the invention, it is thus possible to determine the quality of a liquid with a high degree of accuracy and/or to undertake the monitoring thereof, either continuously or at periodic intervals.

According to the invention, this object can also be fulfilled by further advantageous features disclosed below and in the claims.

In one advantageous configuration, for example, it is provided that the shielding electrode encloses the inner electrode, at least in the region of the insulating element, in an annular manner. This is advantageous, in that any influence of charges upon the inner electrode, associated with the action of electric fields which originate from the insulation of the measuring assembly, specifically from the insulating element, can be effectively suppressed.

Specifically, by such an embodiment, a coaxial shielding can be constituted, which permits particularly effective shielding. Alternatively or additionally, it can be provided here that the inner electrode and the shielding electrode are electrically contacted in a mutually separate manner. Accordingly, charges can be applied to these two electrodes in a mutually separate manner. By use of separate contacting, the respective potential and/or quantity of charge on the electrodes can be adjusted in a mutually independent manner.

In a further advantageous configuration, it is provided that the inner electrode, the outer electrode and the shielding electrode are mutually electrically interconnected, such that active shielding is achieved. Active shielding can be understood here as a configuration wherein a potential of the shielding electrode can be actively adjusted to a potential of the inner electrode. The adjustment of potential is preferably achieved by an operational amplifier. By the adjustment of potential, specifically, synchronization of the potentials of the inner electrode and the shielding electrode can be achieved. Accordingly, charges, or charge displacements which accumulate as a result of the influence acting on the shielding electrode, can be effectively diverted, or additional charges can be delivered, such that the potential of the shielding electrode is constantly adjusted to the potential of the inner electrode. By the adjustment of the potential of the shielding electrode, it is thus prevented that charges accumulate on the inner electrode in response to the influence of electric field displacements in the insulation of the measuring assembly. Error influences are thus effectively suppressed.

According to an advantageous configuration of the invention, it can thus be provided that the shielding electrode is electrically connected to the inner electrode via an impedance converter. A practical configuration of active shielding is specified accordingly.

In order to expand the potential applications of a measuring assembly according to the invention, it can be provided that, according to a further configuration, a measuring gap is constituted between the inner electrode and the outer electrode. The liquid can be introduced into this measuring gap. Additionally or alternatively, it can also be provided that the measuring gap accommodates a flux of the liquid. It is thus specifically possible to monitor a fluid by using a flux measurement, wherein liquid thus continuously flows through the measuring assembly. In these configurations, it is preferred if a seal is constituted between the insulating element and the outer electrode and/or between the insulating element and the shielding electrode. By use of the seals, any down-circuit electronics of the measuring assembly can be effectively sealed vis-à-vis the measuring gap such that, specifically, any penetration of liquid into the electronics can be prevented.

According to a further development, it is particularly advantageous if the shielding electrode, in a cross-sectional plane, specifically in the region of a seal, i.e. for example of the abovementioned seal between the insulating element and the shielding electrode, assumes an annular, and preferably circular external outline. A reliable seating of a sealing element, for example of an O-ring, on the shielding electrode can thus be achieved. This configuration of the shielding electrode moreover advantageously permits, by interaction with the insulating element, the achievement of a particularly compact sealing of the measuring gap in the radial direction.

The shielding electrode can specifically be fed through the insulating element. It can thus be provided that, between a or the abovementioned external outline of the shielding electrode and the insulating element, a seal is constituted.

Additionally, it is particularly advantageous if an outer surface of the shielding electrode, in the region of the insulating element, is configured to a cylindrical design. The shielding electrode can thus be configured for particularly simple axial displacement vis-à-vis the insulating element. Specifically, the cylindrical outer surface of the shielding electrode can constitute a guide with respect to a cylindrical inner surface of the insulating element.

According to a further configuration of the invention, it is particularly advantageous if the inner electrode is configured in two parts, having a first section and a second section. Specifically, the second section can be electrically shielded from the insulating element by the shielding electrode. A two-part configuration of this type permits a more complex design of the inner electrode, wherein a compact structure of the measuring assembly is achieved, specifically in the radial direction, notwithstanding the configuration of the shielding electrode. For example, it is thus possible for the inner electrode to be configured with an external diameter of less than 6 mm.

A further advantage is provided in that, by the adjustment of the length of the first section, the absolute magnitude of the capacitance to be measured can be adjusted, while the outer electrode remains unchanged.

According to a further development of the invention, it is provided that the first section and/or the second section, wholly or partly, is/are electrically insulated from the shielding electrode by a connecting element. It is preferred if the connecting element radially and/or axially secures the first section to the shielding electrode. By the use of such a configuration, firstly, effective electrical insulation between the inner electrode and the shielding electrode can thus be achieved; secondly, the attachment provided by the connecting element ensures that the position of the first section of the inner electrode which, in combination with the outer electrode, can constitute the capacitance to be measured, can be securely defined in relation to the outer electrode. This is important for the control of a clearance between the inner electrode, specifically the first section thereof, and the outer electrode, which is involved in the determination of the capacitance to be measured.

According to a further advantageous configuration, it can be provided that the second section is configured as a bar- or wire-shaped inner conductor. As will be further clarified hereinafter, a particularly compact structure can thus be achieved. It can further be provided that the second section of the inner electrode is configured with an insulating sheathing. This sheathing can specifically be employed for the electrical insulation of the second section of the inner electrode from the shielding electrode.

For the simple installation of the measuring assembly, it is particularly advantageous if the second section is inserted through the shielding electrode, preferably through the connecting element, from the exterior up to the first section of the inner electrode. It can thus specifically be provided that the second section is routed centrally through the connecting element. The second section can thus be specifically oriented through a geometrical center of the connecting element.

The connecting element can thus be configured in a particularly stable manner. The second section can further be electrically insulated from the shielding electrode by an insulating sheathing, or the abovementioned insulating sheathing.

According to a further advantageous configuration, it is provided that the first section comprises contact springs, which electrically contact the inserted second section. In the interests of the simplification of assembly, it is advantageous if the contact springs exert a reset force and/or a retaining force on the inserted first section. In these configurations, firstly, secure assembly can be executed, with no visual controls; secondly, even in the event of the employment of proprietary insulated wires for the second section of the inner electrode, secure contacting can be ensured, further to insertion in the second section of the inner electrode.

According to a further configuration, it can be provided that a seal is configured between the connecting element and the first section and/or between the connecting element and the shielding electrode. It can thus be prevented that the liquid to be measured creeps along the second section of the inner electrode to the down-circuit electronics.

In the interests of the maintenance of maximum compactness in the axial direction, in relation to a longitudinal axis of the inner electrode, it is particularly advantageous if a or the abovementioned seal between the connecting element and the shielding electrode constitutes an inner seal. In an advantageous manner, this inner seal can be axially offset in relation to a or to the abovementioned seal constituted between the insulating element and the shielding electrode. In other words, the inner seal can thus be axially offset in relation to the insulating element. It is particularly preferred if the inner seal is constituted in the region of the measuring gap. As will be further clarified by reference to the drawings, by the axial displacement of the inner seal in the direction of the measuring gap, the insulating element 4, and a recess provided for the insulating element 4, can be restricted in size, such that the dimensions of the measuring assembly in the radial direction, notwithstanding the constitution of the shielding electrode, are not enlarged.

In order to enable the electrically secure operation of the measuring assembly, it is proposed, according to a further configuration, that at least one of the seals constituted on the insulating element seal(s) the liquid in the measuring gap from a closed inner space. Accordingly, in this closed inner space, an electric circuit can preferably be arranged for the achievement of active shielding.

According to a further configuration of the invention, it is provided that the inner electrode comprises a preferably axially and/or radially moveable end. It is thus possible to compensate thermomechanical stresses which can be constituted in response to temperature variations in the inner electrode. The magnitude of the measuring gap can thus be maintained, or can at least be varied in a manner which can be modeled, and thus compensated, using simple models, specifically linear models. It is preferred if the insulating element is a first insulating element, and the moveable end is supported in a second insulating element, preferably by an elastomer. Moreover, in this configuration, the shielding electrode specifically can be securely clamped, preferably in the first insulating element. In the interests of a compact structure, it is further advantageous if the first and the second insulating elements are retained by the outer electrode.

According to a further advantageous configuration, it is provided that the shielding electrode is axially positioned in relation to the outer electrode by a screw connection. To this end, specifically, an external thread can be configured on the shielding electrode. A particularly robust configuration of the measuring assembly vis-à-vis thermal influencing factors is thus disclosed, which permits high accuracy of measurement.

In general, it is advantageous according to the invention if preferably all the elements of the measuring assembly, which are sealed from one another by a respective seal, are configured for axial displacement in relation to one another. In the interests of the accurate axial displacement of the respective elements, screw connections can advantageously be employed. In these configurations, a respective seal can thus be compressible in an axial and/or radial direction by axial loading. This permits, firstly, simple assembly by the interlocking and screw connection of the individual components of the measuring assembly; secondly, the seals can be securely and reliably adjusted by appropriate contact pressures, in a manner which is necessary for the secure operation of the measuring assembly, specifically during the measurement of hot liquids.

BRIEF DESCRIPTION OF THE DRAWINGS

The invention is described in greater detail hereinafter with reference to exemplary embodiments, but is not limited to these exemplary embodiments.

Further exemplary embodiments proceed from the combination of the characteristics of individual or multiple claims for protection with one another and/or with individual or multiple characteristics of the respective exemplary embodiment. Specifically, configurations of the invention can thus proceed from the following description of a preferred exemplary embodiment, in combination with the general description, the claims and the drawings.

In the drawings:

Figure 1:
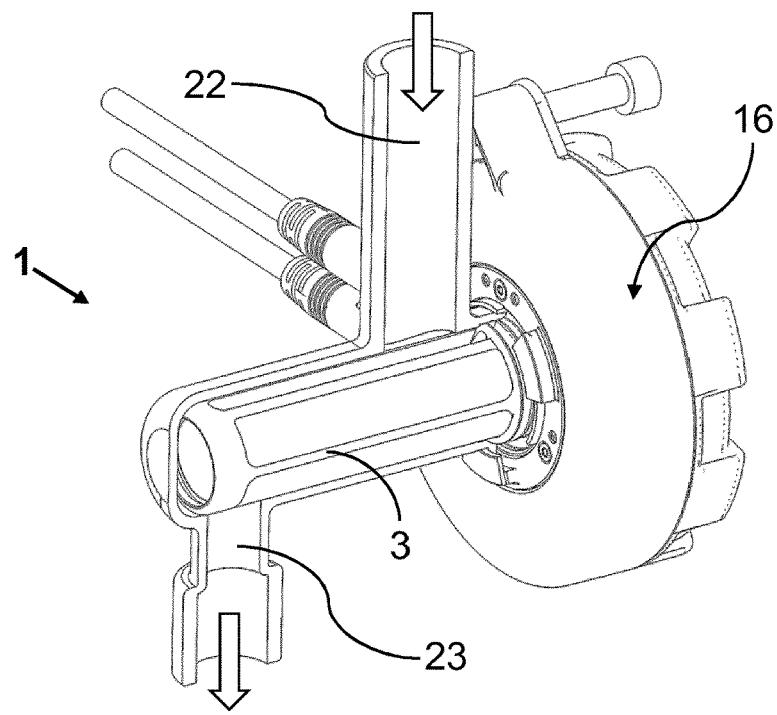
Figure 2:
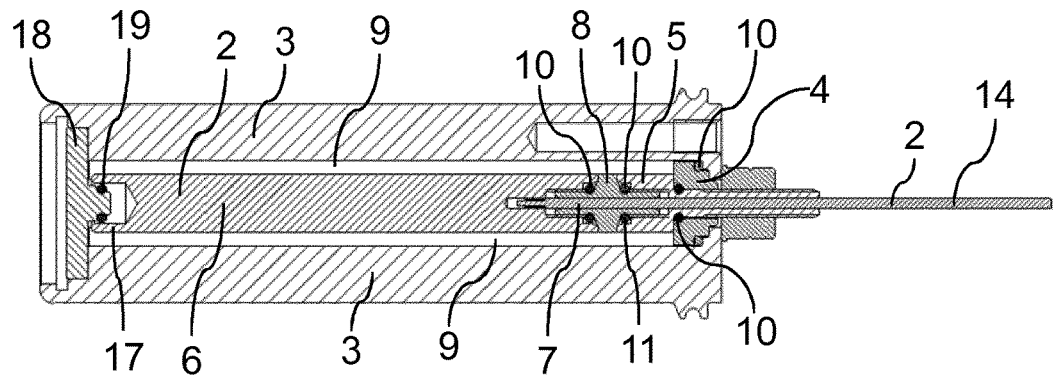
Figure 3:
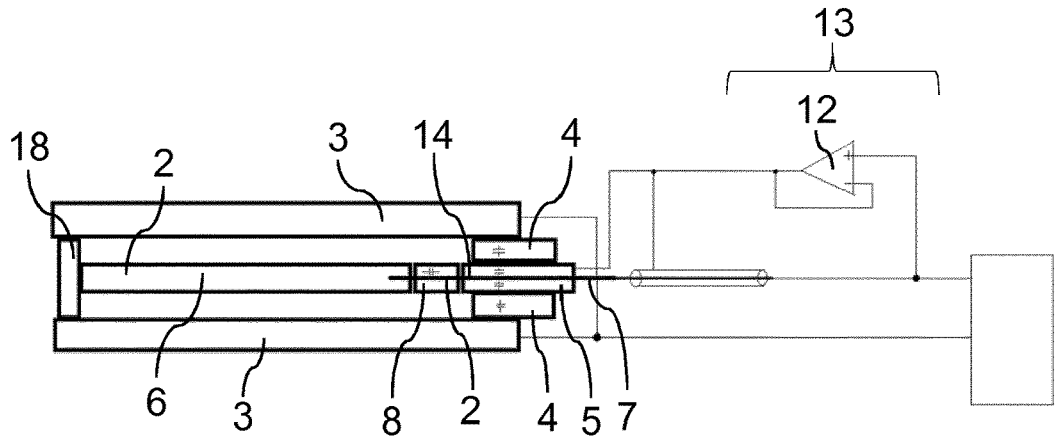
Figure 4:
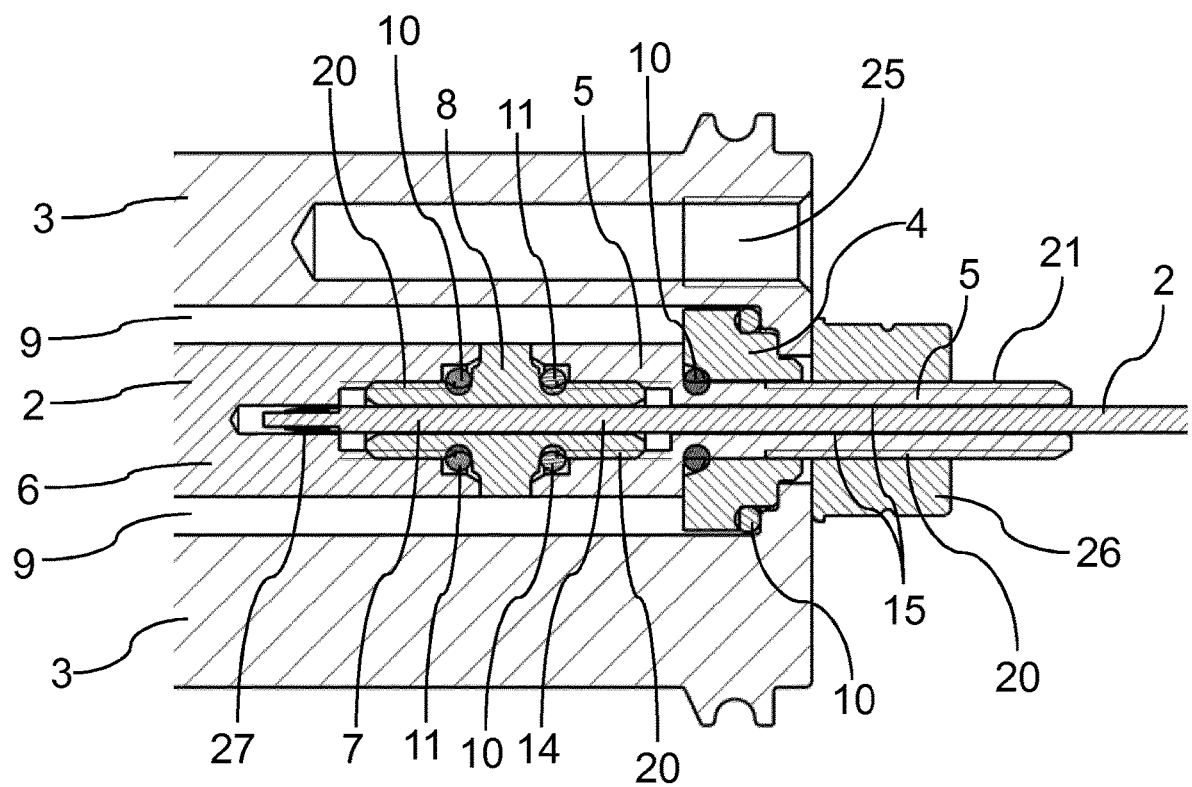
Figure 5:
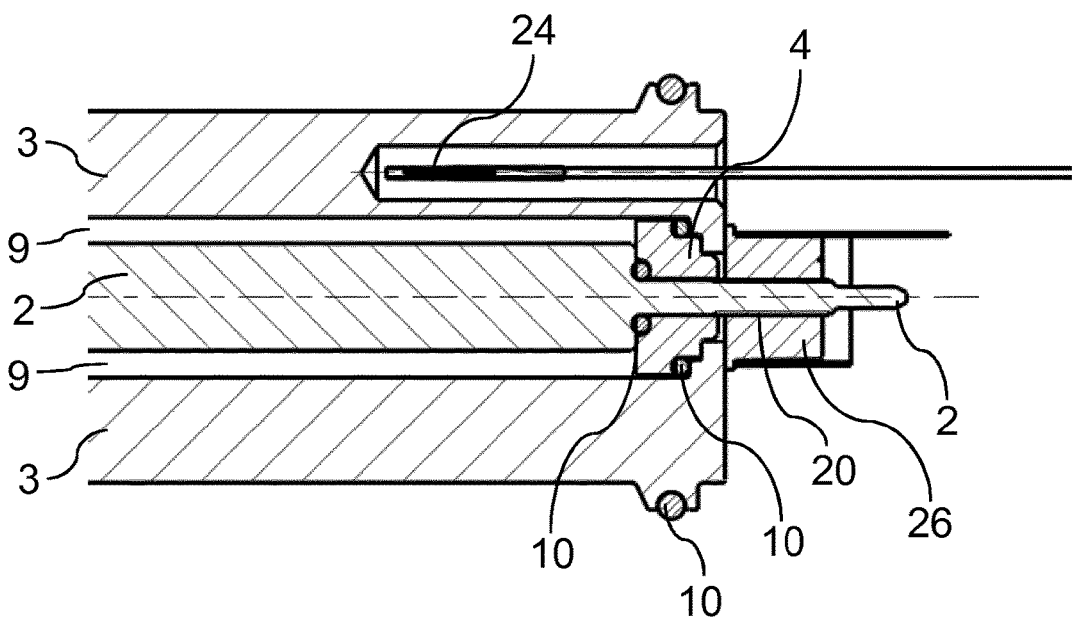

FIG. 1 shows an overall view of a measuring assembly according to the invention, which is integrated in a line of a fryer for the conveyance of oil and/or fat, FIG. 2 shows a detailed longitudinal sectional view of a measuring assembly according to the invention, which shows the internal layout of the measuring electrodes and the insulation employed, FIG. 3 shows a schematic view of the measuring assembly represented in FIG. 2 wherein, at the right-hand edge of the image, an electric circuit diagram of the measuring assembly is reproduced, FIG. 4 shows a section of the illustration from FIG. 2, which represents further details of a measuring assembly according to the invention, and FIG. 5 shows a measuring assembly with no shielding electrode, with reference to which the advantages and differences of a measuring assembly according to the invention can be inferred.

DETAILED DESCRIPTION

FIG. 1 shows a measuring assembly, which is identified overall by the number 1, for the capacitive measurement of a frying oil and/or a frying fat. To this end, the frying oil and/or frying fat is introduced to the measuring assembly 1 by an infeed 22 of an outer electrode 3, and is evacuated from the latter by a discharge 23, such that a throughflow measurement is executed.

As shown in FIG. 2, the outer electrode 3 is constituted by a cylindrical main body. An inner electrode 2 is arranged with a clearance to the outer electrode 3, the longitudinal axis of which coincides with a longitudinal axis of the outer electrode 3. The outer electrode 3 thus concentrically encloses the inner electrode 2. A cylindrical measuring gap 9 is constituted between the inner electrode 2 and the outer electrode 3. This measuring gap 9 incorporates a bubble-free throughflow of the frying oil and/or the frying fat, in both the radial and the axial direction (with respect to the longitudinal axis of the inner electrode 3 in each case).

In the exemplary embodiment represented in FIG. 2, the inner electrode 2 is configured in two parts. A first section 6 of the inner electrode 2, in combination with the outer electrode 3, constitutes the capacitance to be measured across the measuring gap 9. A second section 7 of the inner electrode 2 is configured as a wire with an insulating sheathing 15, and is inserted in a bore in the first section 6. For the electrical contacting of the two sections 6, 7 of the inner electrode 2, contact springs 27 are provided, which exert a retaining force on the inserted second section 7.

The inner electrode 2, more specifically the first section 6 thereof, comprises a moveable end 17, which is supported in a second insulating element 18 in an axially moveable manner, by an elastomer 19. Thus, in the event of temperature variations, the inner electrode 2 can expand in the axial direction, with no impediment. The second insulating element 18 is inserted in a recess in the outer electrode 3, and is retained by the latter.

As shown in FIG. 4, the first section 6 incorporates a bore and an internal thread, into which a connecting element 8 is screwed, wherein a seal 10 which is configured as an O-ring seals the screw connection 20.

In the same manner, a shielding electrode 5, which is configured cylindrically and, in the region of the measuring gap 9, with the same external diameter as the first section 6, is screwed to the connecting element 8 wherein, here again, a seal 10 is configured in the form of an O-ring.

By the two screw connections 20 configured on the connecting element 8, the first section 6 is both radially and axially secured to the shielding electrode 5. The position of the first section 6 of the inner electrode 2 relative to the outer electrode 3 can thus be established with high accuracy by the positioning of the shielding electrode 5 relative to the outer electrode 3 by a further screw connection 20 (using the clamping nut 26). Positional accuracy of this type is necessary for the achievement of a high measuring accuracy, as any variation in the measuring gap 9 results in a defective measuring signal.

To this end, as further shown in FIG. 4, the outer electrode 5 is provided with an external thread 21 such that, by the use of a clamping nut 26, the shielding electrode 5 can be axially positioned in relation to the outer electrode 3 or the insulating element 4. By the axial displaceability of the shielding electrode 5 relative to the insulating element 4, and thus also to the outer electrode 3, it can further be achieved that the seal 10 which is configured between the two elements 4, 5 can be compressed both axially and radially in relation to the longitudinal direction of the inner electrode 2, such that a secure seal can be ensured.

The connecting element 8 is formed of an insulating material, such that the connecting element 8 electrically insulates the shielding electrode 5 from the inner electrode 2, and from both the first section 6 and the second section 7 thereof, as can be seen from the detailed illustration shown in FIG. 4. The shielding electrode 5, in turn, is inserted in a recess in the insulating element 4, whereas the inner electrode 2, more specifically the second section 7, is fed through a central bore in the shielding electrode 5. In other words, the second section 7 of the inner electrode 2 is thus configured as an inner conductor 14 wherein, by a sheathing 15 (c.f. FIG. 4), electrical insulation between the shielding electrode 5 and the second section 7 of the inner electrode 2 is ensured.

In the exemplary embodiment shown in FIG. 2, the shielding electrode 5 encloses the inner electrode 2 in the region of the insulating element 2 in an annular manner, wherein a coaxial shielding is constituted, which shields the inner electrode 2 against the insulating element 4. The shielding electrode 5 is thus securely clamped by a screw connection 20 (c.f. FIG. 4) in a first insulating element 4, which is inserted in a recess in the outer electrode 3 and retained by the latter.

In the example of a measuring assembly with no shielding electrode 5 shown in FIG. 5, variations in permittivity in the insulating element 4 impact directly upon the potential of the inner electrode 2. Such electric field crosstalk in the capacitance to be measured between the inner electrode 2 and the outer electrode 3 is effectively prevented by the provision of the shielding electrode 5.

For the clarification of this electrical shielding, FIG. 3 shows a simplified schematic representation of the measuring assembly from FIG. 2. As can be seen from the electric circuit diagram in the right-hand section of FIG. 3, the inner electrode 2 and the shielding electrode 5 are electrically contacted in a mutually separate manner. The inner electrode 2, more specifically the second section 7 thereof, is thus connected to the input of an operational amplifier 12, whereas the output of the operational amplifier 12 is connected to the shielding electrode 5, which is electrically insulated from the second section 7 by the sheathing 15 (c.f. FIG. 4), which is not represented in FIG. 3.

By the negative feedback of the output voltage of the operational amplifier 12, the latter consistently follows the input voltage applied. By this interconnection, the potential of the shielding electrode 5 is thus actively adjusted to the potential of the inner electrode 2. It is thus ensured that no electrical voltage can be constituted between the two electrodes 2 and 5. In other words, the shielding electrode 5 is thus electrically connected to the inner electrode 2 via an impedance converter 13 (embodied by the interconnection of the operational amplifier 12).

As indicated by the capacitor symbols in FIG. 3, stray capacitances are present, which are constituted by the insulating element 4. However, on the grounds of the shielding electrode 5, and the abovementioned electric circuit, electric fields produced by dielectric displacements in these stray capacitances cannot impact upon the inner electrode 2, more specifically upon the second section 7 thereof. Likewise, the capacitance present between the shielding electrode 5 and the second section 7, associated with the sheathing 15, cannot interfere with the measurement of the permittivity of the frying oil and/or of the frying fat in the measuring gap 9, as the electrical potentials of these two electrodes 5, 7 are synchronized by the impedance converter.

An analogous case applies to the stray capacitance which is constituted between the first section 6 of the inner electrode 2 and the shielding electrode 5, conveyed through the insulating connecting element 8. The first section 6 is thus at the same electrical potential as the second section 7, and thus of the shielding electrode 5. As the electrical interference effects of the connecting element 8 are thus entirely eliminated, the latter can be formed, for example, of a cost-effective plastic, the permittivity of which per se can show a comparatively high temperature dependence, with no resulting corruption of measurement.

As shown in further detail in FIG. 4, the second section 7 of the inner electrode 2, which is configured as a wire-shaped inner conductor 14 and provided with an insulating sheathing 15, is initially inserted from the exterior through the shielding electrode 5 and the connecting element 8, and into the first section 6 of the inner electrode 2. In order to prevent any encroachment of frying oil and/or frying fat, originating from the measuring gap 9 and progressing along said inner conductor to any down-circuit electronics, an inner seal 11 is therefore configured between the connecting element 8 and the outer electrode 5. This inner seal 11 is constituted by the two abovementioned O-rings, which are fitted to the connecting element 8.

As shown in the longitudinal section represented in FIG. 4, the inner seal 11, in the axial direction, is arranged with an offset in relation to the insulating element 4, or in relation to the seal 10 configured on the insulating element 4. By use of the axial offset, valuable structural space in the radial direction is thus economized such that, specifically, the external diameter of the outer electrode 3 can be preserved, notwithstanding the constitution of the shielding electrode 5.

A further advantage is provided, in that it is possible to omit the constitution of concentrically configured seals which, in any event, introduce an element of mechanical play which is detrimental to high measuring accuracy. By the spatial separation of seals, specifically, the inner seal can be configured to correspondingly larger dimensions, thus permitting the more effective sealing of any surface roughness of the components to be sealed. The only disadvantage of the axial offset of the inner seal 11 represented in FIG. 4 is that the latter is configured in the region of the measuring gap 9, such that the part of the measuring gap 9 which lies between the shielding electrode 5 and the outer electrode 3 cannot be employed for the measurement of liquid.

By the abovementioned screw connection 20, as also represented in FIG. 4 and constituted by the clamping nut 26 and the external thread 21 of the shielding electrode 5, the two seals 10 configured on the insulating element 4 can be axially loaded in a controlled manner, and thus axially and/or radially compressed in a controlled manner. These seals 10 thus seal the liquid in the measuring gap 9 from an enclosed inner space, which is indicated in FIG. 1 by the reference number 16, in which the electric circuit illustrated in FIG. 3 for the execution of active shielding is accommodated.

The outer electrode 3, as illustrated in FIG. 4, can incorporate a bore 25 for the accommodation of a temperature sensor 24, as illustrated in FIG. 5.

In summary, for the enhancement of the measuring accuracy of an electrical measuring assembly 1 for the capacitive measurement of a liquid, having an inner electrode 2 and an outer electrode 3 arranged concentrically thereto, it is provided that a shielding electrode 5 is arranged between the outer electrode 3 and the inner electrode 2, wherein, preferably, by a corresponding electrical interconnection, a potential of the shielding electrode 5 can be actively adjusted to a potential of the inner electrode 2, such that electric fields which are generated by dielectric displacements in stray capacitances are effectively shielded from the inner electrode, and thus from the capacitance to be measured. To this end, the invention specifically proposes a two-part configuration of the inner electrode 2, with mutually axially displaceable sections 6 and 7.

LIST OF REFERENCE NUMBERS

1 Measuring assembly
2 Inner electrode
3 Outer electrode
4 (First) insulating element
5 Shielding electrode
6 First section
7 Second section
8 Connecting element
9 Measuring gap
10 Seal
11 Inner seal
12 Operational amplifier
13 Impedance converter
14 Inner conductor
15 Sheathing
16 Inner space
17 End (of inner electrode)
18 Second insulating element
19 Elastomer
20 Screw connection
21 External thread
22 Infeed
23 Discharge
24 Temperature sensor
25 Bore
26 Clamping nut
27 Contact springs

The invention claimed is:

1. An electrical measuring assembly (1) for the capacitive measurement of a liquid, the electrical measuring assembly comprising:
   an outer electrode (3),
   an inner electrode (2) which is arranged concentrically to and surrounds the outer electrode (3),
   an insulating element (4) which electrically insulates the inner electrode (2) from the outer electrode (3), and
   a shielding electrode (5) arranged between the inner electrode (2) and the insulating element (4), which shields the inner electrode (2) from the insulating element (4),
   wherein all the elements of the measuring assembly (1), which are sealed from one another by a respective seal (10), are configured for axial displacement in relation to one another, by screw connections (20), such that the respective seal (10) is compressible in at least one of an axial or radial direction by axial loading.

2. The measuring assembly (1) as claimed in claim 1, wherein the shielding electrode (5) encloses the inner electrode (2), at least in a region of the insulating element (4), in an annular manner, providing a coaxial shielding.

3. The measuring assembly (1) as claimed in claim 1, wherein the inner electrode (2), the outer electrode (3) and the shielding electrode (5) are mutually electrically interconnected, such that active shielding is achieved, and a potential of the shielding electrode (5) is actively adjustable to a potential of the inner electrode (2).

4. The measuring assembly (1) as claimed in claim 1, further comprising a measuring gap (9) located between the inner electrode (2) and the outer electrode (3), into which the liquid is at least one of adapted to be introduced or through which the liquid is adapted to flow.

5. The measuring assembly (1) as claimed in claim 1, wherein the inner electrode (2) is configured in two parts, having a first section (6) and a second section (7), and the second section (7) is electrically shielded from the insulating element (4) by the shielding electrode (5).

6. The measuring assembly (1) as claimed in claim 5, wherein at least one of the first section (6) or the second section (7), wholly or partly, is electrically insulated from the shielding electrode (5) by a connecting element (8).

7. The measuring assembly (1) as claimed in claim 6, wherein at least one of: the second section (7) is configured as a bar- or wire-shaped inner conductor (14), an insulating sheathing (15) is provided on the inner conductor (14), or the second section (7) is inserted through the shielding electrode (5) from the exterior up to the first section (6).

8. The measuring assembly (1) as claimed in claim 7, wherein at least one of: the second section (7) is fed centrally through the connecting element (8), or the second section (7) is electrically insulated from the shielding electrode (5)_by the insulating sheathing (15).

9. The measuring assembly (1) as claimed in claim 6, wherein the first section (6) comprises contact springs (27), which electrically contact the second section (7), and the contact springs (27) exert at least one of a reset force or a retaining force on the inserted first section (6).

10. The measuring assembly (1) as claimed in claim 9, further comprising a seal (10) between the connecting element (8) and the shielding electrode (5), and an inner seal (11) axially offset in relation to the seal (10) between the insulating element (4) and the shielding electrode (5), or axially offset in relation to the insulating element (4).

11. The measuring assembly (1), as claimed in claim 10, wherein at least one of the seals (10) on the insulating element (4) is adapted to seal the liquid in the measuring gap (9) from a closed inner space (16).

12. The measuring assembly (1) as claimed in claim 11, further comprising an electric circuit for achievement of active shielding is arranged in said inner space (16).

13. The measuring assembly (1) as claimed in claim 10, wherein the inner seal (11) is constituted in the region of the measuring gap (9).

14. The measuring assembly (1) as claimed in claim 6, further comprising a seal (10) at least one of between the connecting element (8) and the first section (6) or between the connecting element (8) and the shielding electrode (5).

15. The measuring assembly (1) as claimed in claim 6, wherein the connecting element (8) at least one of radially or axially secures the first section (6) to the shielding electrode (5).

16. The measuring assembly (1) as claimed in claim 1, further comprising a screw connection (20), and the shielding electrode (5) is specifically positioned on an external thread (21) of the shielding electrode (5) by the screw connection, axially in relation to the outer electrode (3).

17. The measuring assembly (1) as claimed in claim 1, wherein the inner electrode (2) and the shielding electrode (5) are electrically contacted in a mutually separate manner, such that charges are applicable to the shielding electrode in a mutually separate manner.

18. The measuring assembly (1) as claimed in claim 1, wherein the shielding electrode (5) is electrically connected to the inner electrode (2) via an impedance converter (13).

19. The measuring assembly (1) as claimed in claim 1, further comprising a seal (10) at least one of between the insulating element (4) and the outer electrode (3) or between the insulating element (4) and the shielding electrode (5).

20. The measuring assembly (1) as claimed in claim 1, wherein the shielding electrode (5), in a cross-sectional plane, has an annular external outline.

21. An electrical measuring assembly (1) for the capacitive measurement of a liquid, the electrical measuring assembly comprising:
   an outer electrode (3),
   an inner electrode (2) which is arranged concentrically to and surrounds the outer electrode (3),
   an insulating element (4) which electrically insulates the inner electrode (2) from the outer electrode (3), and
   a shielding electrode (5) arranged between the inner electrode (2) and the insulating element (4), which shields the inner electrode (2) from the insulating element (4),
   wherein the inner electrode (2) comprises a moveable end (17), the insulating element (4) comprises a first insulating element (4) and the moveable end is supported in a second insulating element (18), and the shielding electrode (5).

22. The measuring assembly (1) as claimed in claim 21, wherein the first and the second insulating element (4, 18) are retained by the outer electrode (3).

* * * * *